(12) United States Patent
Vazeen

(10) Patent No.: US 7,018,410 B1
(45) Date of Patent: Mar. 28, 2006

(54) ACCOMMODATING INTRAOCULAR LENS

(76) Inventor: Mehdi Vazeen, 412 W. John St., Carson City, NV (US) 89703

( * ) Notice: Subject to any disclaimer, the term of this patent is extended or adjusted under 35 U.S.C. 154(b) by 0 days.

(21) Appl. No.: 10/213,705

(22) Filed: Aug. 5, 2002

(51) Int. Cl.
*A61F 2/16* (2006.01)

(52) U.S. Cl. .................................. 623/6.37; 623/6.39

(58) Field of Classification Search ...... 623/6.37–6.54, 623/6.22, 6.19, 6.2, 6, 6.11
See application file for complete search history.

(56) References Cited

U.S. PATENT DOCUMENTS

| | | | |
|---|---|---|---|
| 4,409,691 A | 10/1983 | Levy | |
| 4,485,499 A | 12/1984 | Castleman | |
| 4,804,361 A * | 2/1989 | Anis | 623/6.42 |
| 4,842,600 A * | 6/1989 | Feaster | 623/6 |
| 4,842,602 A * | 6/1989 | Nguyen | 623/6.54 |
| 4,863,463 A * | 9/1989 | Tjan | 623/6 |
| 4,888,012 A | 12/1989 | Horn et al. | |
| 4,994,082 A | 2/1991 | Richards et al. | |
| 5,133,750 A | 7/1992 | Momose et al. | |
| 5,152,789 A * | 10/1992 | Willis | 623/6 |
| 5,366,501 A * | 11/1994 | Langerman | 623/6.42 |
| 5,476,514 A | 12/1995 | Cumming | |
| 5,571,177 A | 11/1996 | Deacon et al. | |
| 5,628,798 A | 5/1997 | Eggleston et al. | |
| 5,766,244 A * | 6/1998 | Binder | 623/6 |
| 6,013,101 A * | 1/2000 | Israel | 623/6 |
| 6,051,024 A | 4/2000 | Cumming | |
| 6,117,171 A | 9/2000 | Skottun | |
| 6,176,878 B1 | 1/2001 | Gwon et al. | |
| 6,179,870 B1 | 1/2001 | Sourdille et al. | |
| 6,200,343 B1 | 3/2001 | Anschutz | |
| 6,261,321 B1 * | 7/2001 | Kellan | 623/6.51 |
| 6,398,809 B1 * | 6/2002 | Hoffmann et al. | 623/6.49 |
| 6,409,762 B1 * | 6/2002 | Pynson et al. | 623/6.39 |
| 6,533,813 B1 * | 3/2003 | Lin et al. | 623/6.37 |
| 6,660,035 B1 * | 12/2003 | Lang et al. | 623/6.37 |
| 2001/0016771 A1 | 8/2001 | Cumming | |
| 2002/0087210 A1 * | 7/2002 | Stenger et al. | 623/6.49 |
| 2002/0151973 A1 * | 10/2002 | Arita et al. | 623/6.22 |
| 2003/0055499 A1 * | 3/2003 | Nguyen et al. | 623/6.49 |
| 2003/0135271 A1 * | 7/2003 | Bandhauer | |

FOREIGN PATENT DOCUMENTS

| | | |
|---|---|---|
| WO | WO 92/15260 | 3/1992 |
| WO | WO 01/05327 | 7/2000 |

* cited by examiner

*Primary Examiner*—Corrine McDermott
*Assistant Examiner*—Cheryl Miller
(74) *Attorney, Agent, or Firm*—Theodore J. Bielen, Jr.

(57) ABSTRACT

An accommodating intraocular lens utilizing an optical element for correcting the vision of a patient. The optical element is positioned in the open capsular bag following an extra-capsular surgical procedure and phakoemulsification of the clouded natural lens. The optical element is adjusted anteriorly and posteriorly by a plurality of arms that are linked to the open capsular bag held by the zonular system of the eye.

5 Claims, 3 Drawing Sheets

ACCOMMODATING INTRAOCULAR LENS

BACKGROUND OF THE INVENTION

The present invention relates to a novel and useful accommodating intraocular lens.

Intraocular lenses have been implanted in eyes following cataract surgery for a number of years. A conventional intraocular lens is intended to replace the natural lens which has been removed due to such cataract condition. Surgical techniques have evolved over the years to performance of an extra-capsular procedure. That is to say, the capsule which held the removed natural lens is retained in the posterior chamber of the eye, minus an excised frontal portion. The result is a capsular bag connected to the ciliary muscle by a multiplicity of zonules, commonly referred to as the zonular system. In this manner, vitreous humor is maintained in the posterior chamber of the eye and the inserted intraocular lens is confined or fixed in the eye for use.

Unfortunately, intraocular lenses do not provide the patient with near and far vision, since intraocular lenses do not react to the contraction and relaxation of the zonular system. This ability is normally referred to as "accommodation". Thus, a patient must be fitted with corrective glasses in order to perform tasks associated with near and far vision, e.g. reading and driving a vehicle.

In the past, accommodating intraocular lenses have been proposed, but have gained limited success.

For example, U.S. Pat. Nos. 4,485,499 and 6,200,343 B1 show intraocular lenses with resilient curved open loops to fix and intraocular lens in the posterior chamber of the eye.

International patent application WO 92/15260 reveals an intraocular lens with a pair of loops that essentially encircle the lens to aid in the fixation of the same to the posterior chamber of the eye when compressed.

U.S. Pat. No. 5,133,750 shows an intraocular lens constructed of synthetic sapphire which includes a quartet of arms to hold the lens in place.

International application WO 01/0532782 describes an intraocular lens for pediatric use which employs a pair of curved arms that completely encircle the lens to prevent the formation of a secondary cataract.

U.S. Pat. No. 5,571,177 indicates an intraocular lens with a fixation member that can be altered after insertion to control the repositioning of the optic portion of the eye.

U.S. Pat. No. 5,628,798 teaches an adjustable and removable intraocular lens having a portion which may be changed, adjusted, or modified after insertion.

U.S. Pat. No. 6,117,171 illustrates an encapsulated accommodating intraocular lens having two spaces separated by a transparent flexible membrane. Altering the curvature of the membrane alters the overall optical power of the lens.

U.S. Pat. No. 4,888,012 shows an intraocular lens assembly in which the lens is formed of elastic material which is extended or compressed to change the shape of the optical portion to accommodate with alterations in the tension of the ciliary muscle of the eye.

U.S. Pat. No. 6,176,878 B1 poses an accommodating intraocular lens having an optic that is connected to a flexible disc that moves the optic inwardly and outwardly according to changes in the tension of the ciliary muscle.

U.S. Pat. Nos. 4,409,691, 4,994,082, 5,476,514, 6,179,870 B1, and publication U.S. 2001/0016771 A1 describe accommodating intraocular lens structures which employ flexible arms that move the optical portion of an intraocular lens posteriorly or anteriorly with ciliary muscle changes and tension.

An optically accurate accommodating intraocular lens would be a notable advance in the medical field of eye care.

BRIEF SUMMARY OF THE INVENTION

In accordance with the present invention a novel and useful accommodating intraocular lens is herein provided.

The lens of the present invention utilizes an optical element which is chosen to correct the vision of a particular individual following removal of the natural lens possessing a cataract condition and performance of an anterior capsulotomy.

Support means is employed for positioning the optical element in the open capsular bag at the posterior chamber of the eye. Such support means may take the form of an elongated member which extends along the periphery of the interior of the open capsular bag. The elongated member may be curved and terminate, at its end portions, with an enlargement. Such support means may include a pair of such elements diametrically opposed to one another within the capsular bag. The support means may also be formed with a plurality of flanges which are intended to extend from the elongated member in the vicinity of the anterior surface of the capsular bag. Bonding of the support means to the capsular bag occurs through the natural growth of fibrous tissue.

Adjustment means is also included in the present invention for effecting movement of the optical element anteriorly and posteriorly. The adjustment means utilizes a plurality of rotatable flexible arms which depend from the elements of the support means. The plurality of rotatable flexible arms may be curved and lie spaced from one another about the peripheral portion of the optical element. The plurality of rotatable arms are linked to the open capsular bag held by the zonular system of the eye. Such linking takes place through the support means elements such that forces exerted by the capsular bag on the support means is transferred to the plurality of rotatable arms. Relaxation of the zonular system will cause the capsular bag to collapse and force the rotation of the plurality of arms to move the optical element anteriorly. Likewise, tensioning of the zonular system will cause the plurality of rotatable arms to move the optical element posteriorly. Of course, the support means remains fixed to the capsular bag does not rotated with the plurality of rotatable arms, but generally serves as an anchor for the same.

It may be apparent that a novel and useful accommodating intraocular lens has been hereinabove described.

It is therefore an object of the present invention to provide an accommodating intraocular lens which provides near and far vision to a patient based on the natural relaxation and tensioning of the zonular system.

Another object of the present invention is to provide an accommodating intraocular lens which can be easily implanted in an eye following extra-capsular cataract surgery.

A further object of the present invention is to provide an accommodating intraocular lens which prevents secondary surgical procedures to correct focusing characteristics of intraocular lenses.

Another object of the present invention is to provide an accommodating intraocular lens which eliminates the need for spectacles to provide a patient receiving an implanted intraocular lens with the ability of attain near and far vision ability.

Yet another object of the present invention is to provide an accommodating intraocular lens which correctly and accurately transmits the force or movements of the capsular bag originating in the zonular system to be transmitted to the optical component of the lens of the present invention.

The invention possesses other objects and advantages especially as concerns particular characteristics and features thereof which will become apparent as the specification continues.

For a better understanding of the invention reference is made to the following detailed description of the preferred embodiments thereof which should be referenced to the prior described drawings.

DETAILED DESCRIPTION OF THE PREFERRED EMBODIMENTS OF THE INVENTION

Various aspects of the present invention will evolve from the following detailed description of the preferred embodiments thereof which should be referenced to the prior described drawings.

Figure 1:
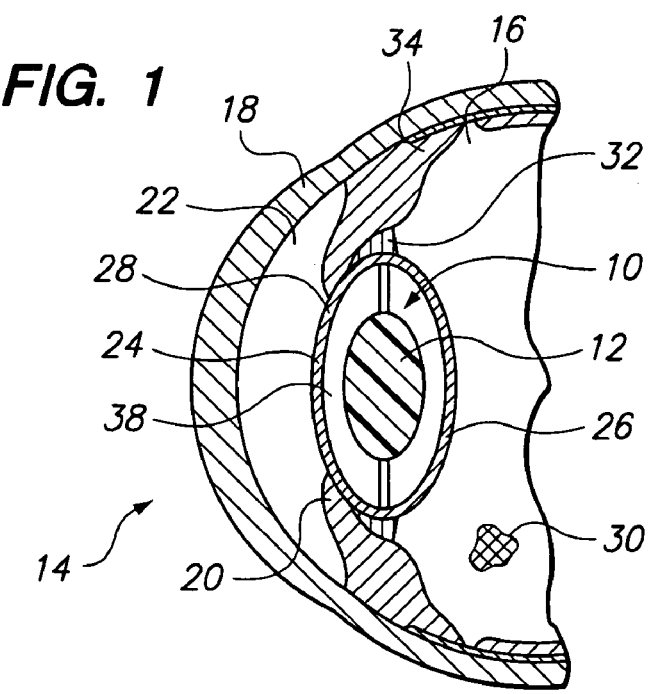
FIG. 1 is a sectional view of the intraocular lens of the present invention implanted in an eye.

The invention as a whole is shown in the drawings by reference character 10. Intraocular lens 10 includes as one of its portions an optical element 12. Optical element 12 takes the form of a crystalline lens composed of any suitable tissue compatible material such as polymethyl methacrylate, polysulfone, hydrogel, silicone, and the like. Optical element 12 is employed to replace the natural lens which has been removed as a result of cataract surgery. The optical properties of element 12 are chosen to correct the vision of a patient in a normal range. Prior art intraocular lenses using similar optical elements require the patient to be fitted with corrective glasses in order to achieve near and far vision. Optical element 12 is shown in FIG. 1 as being implanted in eye 14, specifically in posterior chamber 16 thereof. Eye 14 includes cornea 18 and iris 20 which generally provide the confines to anterior chamber 22. Pupil 24 serves as the adjustable circular opening between anterior chamber 22 and posterior chamber 16 which permits light passing through cornea 18 to travel through optical element 12 and, eventually, to the retina (not shown). Capsular bag 26 represents the remnant of the natural capsule and includes an opening 28 adjacent pupil 24. Capsular bag 26 is employed to hold or fixate intraocular lens 10 into prevent the movement of vitreous humor 30 normally found in the posterior anterior chamber 16. Capsular bag 26 is resilient and is supported in place by zonules 32. Zonules 32 directly connect to ciliary muscle 34. Ciliary muscle 34 and zonules 32 comprise the zonular system 36 which, in turn, stretches and collapses capsular bag 26 during the natural focusing process of eye 14.

Figure 2:
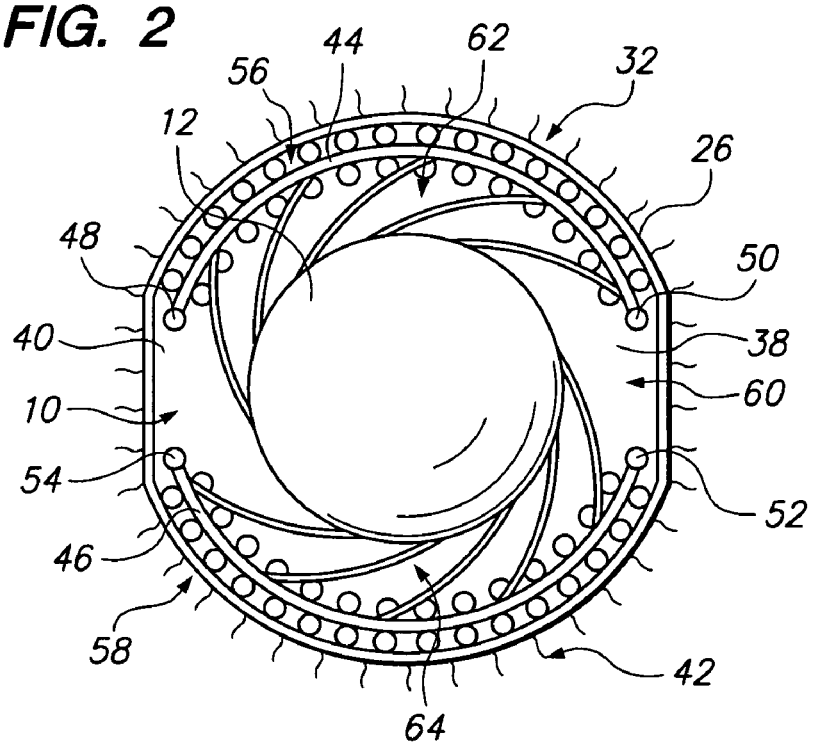
FIG. 2 is a front elevational view of the implanted lens depicted in FIG. 1.

Turning to FIG. 2, it may be observed that intraocular lens 10 is depicted as lying within chamber 38 of capsular bag 26. Chamber 38 is formed by inner wall 40 of capsular bag 26. Lens 10 is also provided with support means 42 for positioning optical element 12 within chamber 38 of capsular bag 26. Support means 42 includes elongated curved members 44 and 46 which are of generally semicircular configuration. Enlargements 48, 50, 52 and 54 cap the ends of elongated members 44 and 46. A plurality of flanges 56, depicted as circular springs in FIG. 2, are connected to elongated members 44 and 46 such that certain of such flanges lie directly against wall 40 of capsular bag 26. After implantation of lens 10, fibrous tissue between capsular bag 26 and plurality of flanges 56 grows and holds the elongated members 44 and 46 in place, as depicted in FIG. 2. It should be understood that plurality of zonules 32 depicted in FIG. 2 are directly connected to ciliary muscle 34 shown in FIG. 1.

Adjustment means 58 is also illustrated in FIG. 2. Adjustment means takes the form of a plurality of rotatable flexible arms 60 which link elongated members 44 and 46 to optical element 12. It should be realized that plurality of rotatable arms also serve as a portion of support means 42 for optical element 12. As illustrated in FIG. 2, plurality of rotatable arms 60 include a first set 62 associated with elongated member 44 and a second set 64 associated with elongated member 46. Although five rotatable arms are indicated as being associated with each elongated member, 44, 46 a lesser or greater number may be employed in the present invention.

Figure 3:
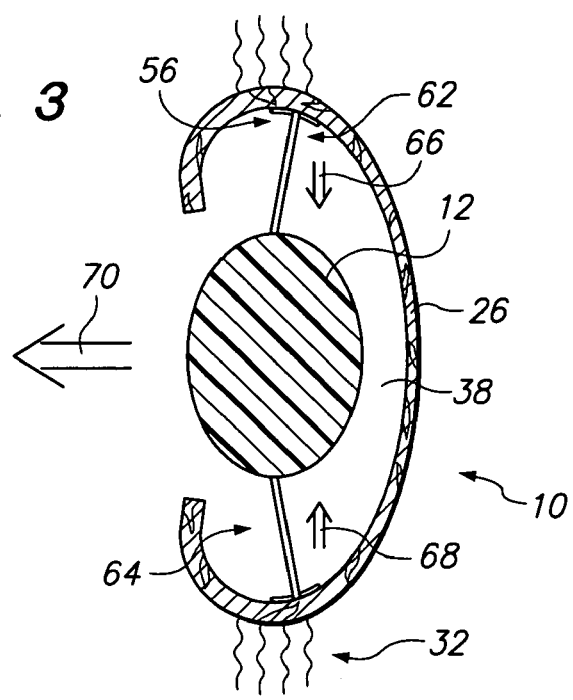
FIG. 3 is a sectional schematic view showing anterior movement of the optical element of the lens of the present invention with relaxation of the zonules.
Figure 4:
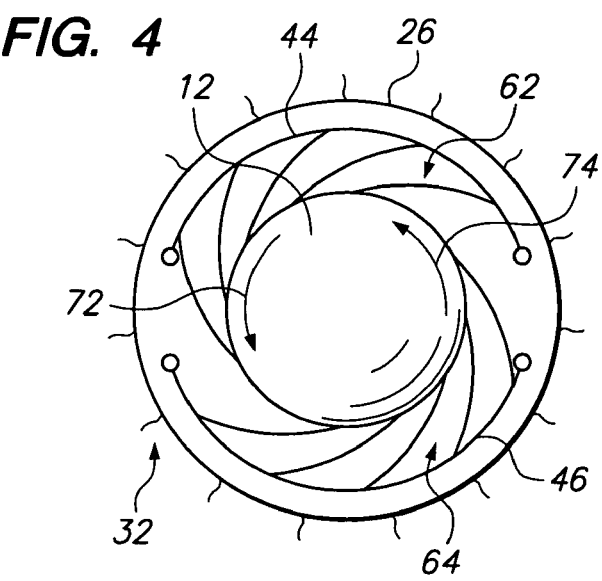
FIG. 4 is a front elevational schematic view of the lens moved anteriorly as shown in FIG. 3.
Figure 5:
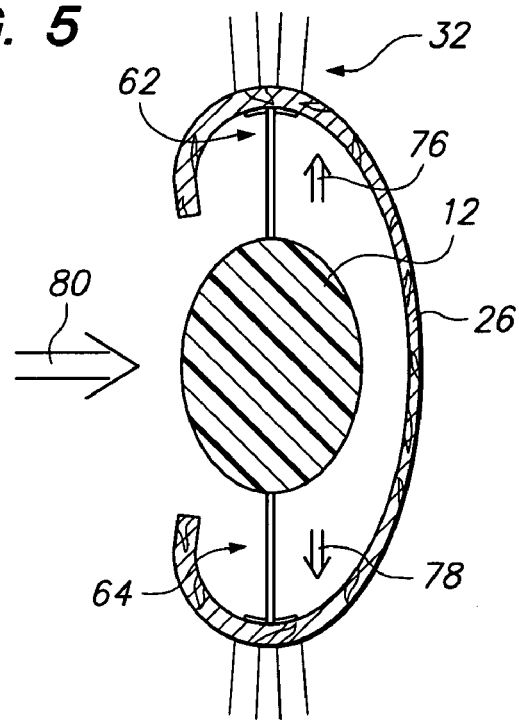
FIG. 5 is a sectional schematic view of the lens of the present invention moving posteriorly with tensioning of the zonules.
Figure 6:
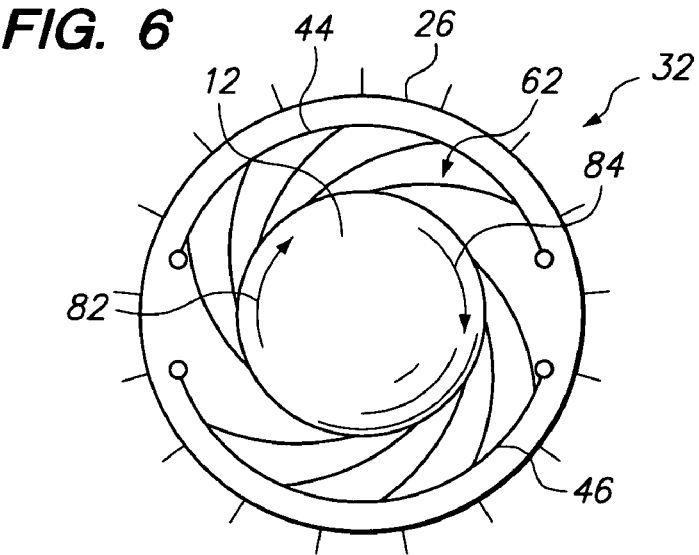
FIG. 6 is a schematic front elevational view of the lens moved posteriorly as depicted in FIG. 5.

In operation, intraocular lens 10 is implanted in eye 14 following cataract surgery resulting in capsular bag 26 shown in FIGS. 1, 3, and 5. FIGS. 3–6 represent the dynamics of intraocular lens 10 within eye 14. For example, FIG. 3 shows the relaxing of zonules 32 causing the partial collapsing of capsular bag 26 according to directional arrows 66 and 68. Such collapsing of capsular bag 26 forces optical element 12 anteriorly according to directional arrow 70. With reference to FIG. 4, it may be observed that sets of plurality of flexible arms 62 and 64 rotate counter clockwise when viewing optical element 12 from the left side of FIG. 3. Elongated members 44 and 46 do not move since they are fixed to capsular bag 26 by fibrous growth. Of course, lens or optical element 12 also rotates slightly according to directional arrows 72 and 74. FIG. 5 illustrates the opposite movement of optical element 12 where plurality of zonules have tensioned causing capsular bag to stretch according to directional arrows 76 and 78. Capsular bag exerts a pulling force on flexible arm sets 62 and 64 moving optical element 12 posteriorly according to directional arrow 80. FIG. 6 illustrates the clockwise turning of optical element 12 according to directional arrows 82 and 84 when optical element is viewed in the same manner as that depicted in FIG. 4.

While in the foregoing, embodiments of the present invention have been set forth in considerable detail for the purposes of making a complete disclosure of the invention, it may be apparent to those of skill in the art that numerous changes may be made in such detail without departing from the spirit and principles of the invention.

What is claimed is:

1. An accommodating intraocular lens for implantation into an eye having an open capsular bag held by a zonular system, comprising:
   a. an optical element;
   b. support means intended for positioning said optical element in the open capsular bag of the posterior chamber of the eye; and
   c. adjustment means for effecting movement of said optical element anteriorly and posteriorly, said adjustment means comprising a plurality of balanced rotatable arms, each of said plurality of balanced rotatable arms being fixed at one end thereof relative to the optical element, each of said plurality of balanced rotatable arms intended for rotation relative to the open capsular bag and for being linked to the open capsular bag held by the zonular system, said plurality of balanced rotatable arms intended for rotating said optical element in one direction relative to the open capsular bag and moving said optical element anteriorly and axially upon relaxation of the zonular system, and said plurality of balanced rotatable arms intended for rotating said optical element in another direction relative to the open capsular bag and moving said optical element posteriorly and axially upon tensioning of the zonular system, said axial movement of said optical element anteriorly and posteriorly being adjunctive to any movement of the capsular bag, said support means comprising an elongated member extending along the periphery of the open capsular bag, said plurality of balanced rotatable arms being connected to said elongated member, and further comprising a multiplicity of flanges extending from said elongated member, said flanges comprising spring members.

2. The intraocular lens of claim 1 in which each of said plurality of balanced rotatable arms are curved.

3. The intraocular lens of claim 1 in which said elongated member comprises a first elongated member, and which further comprises a second elongated member, said plurality of balanced rotatable arms further comprising a first set of arms and a second set of arms, said first set of balanced rotatable arms being connected to said first elongated member, and said second set of balanced rotatable arms being connected to said second elongated member.

4. The intraocular lens of claim 1 in which said elongated member is curved.

5. The intraocular lens of claim 1 in which said elongated member includes at least one end, said one end of said elongated member including an enlargement.

* * * * *